United States Patent [19]

Sudol

[11] Plant 4,354

[45] Dec. 26, 1978

[54] MINIATURE MOSS ROSE PLANT

[75] Inventor: Julia K. Sudol, Alhambra, Calif.

[73] Assignee: Armstrong Nurseries, Inc., Ontario, Calif.

[21] Appl. No.: 864,933

[22] Filed: Dec. 27, 1977

[51] Int. Cl.[2] ..... A01H 5/00

[52] U.S. Cl. ..... Plt./8

[58] Field of Search ..... Plt./8

*Primary Examiner*—Robert E. Bagwill

*Attorney, Agent, or Firm*—Andrew R. Klein

[57] ABSTRACT

A miniature hybrid rose plant of the moss variety, which blooms almost continuously through the growing season, and bears double flowers with 35 to 50 petals and 2 to 10 petaloids. Its ovoid to urn-shaped buds and flowers are off-white in color. The plant bears many single and branched moss-scented stipitate glands on its peduncles, buds, sepals and hips. It has viable pollen and sets hips. The flowers are of average size for roses of the miniature category.

1 Drawing Figure

This invention relates to a new variety of rose plant of the hybrid miniature moss class. The plant is a dwarf bush outdoor seedling, the hardiness of which has not yet been tested, grown primarily for cut flowers and for garden decoration. For purposes of varietal identification, it has been given the denomination of "Aronemo".

The seed parent was "Fairy Moss" (U.S. Plant Pat. No. 3,083). That plant was open pollinated, so that the identity of the pollen parent is unknown. However, the new variety maintains its distinguishing characteristics through succeeding propagations by cuttings and by budding.

The plant herein described was grown in Ontario, Calif., and the description relates to plants grown in that region. Since the plant is of the miniature class, comparative terms relate to other miniature varieties.

The new cultivar differs from its seed parent "Fairy Moss" primarily in the nature of its blooms and flowers. These are nearly white, whereas buds and flowers of the seed parent are deep pink. Furthermore, the new cultivar bears double flowers comprising 35 to 50 petals plus 2 to 10 petaloids, while its seed parent is semi-double, usually with less than half as many petals.

Since the pollen parent has not been identified, no comparison with it can readily be made. However, as noted above, the characteristics of the new cultivar persist under asexual propagation and the plant itself is unique, so far as presently known.

The accompanying drawing illustrates the plant in color and shows the flowering thereof from bud to full bloom. For comparative purposes, a ruler showing inches and centimeters is displayed beside the flower.

Throughout this specification, color names beginning with a small letter signify that the name of that color, as used in common speech, is aptly descriptive. Color names beginning with a capital letter designate values based upon the Nickerson Color Fan, put out by Munsell Color Co.

FLOWER

The flowers are sometimes borne singly, but usually three or more to a stem, in irregular clusters on normal short to long stems. The quantity of bloom with respect to roses grown outdoors is abundant, and is almost continuous throughout the growing season, whereas many moss roses bloom only in the Spring. The blooms have a slight musk fragrance.

Bud

The peduncles are of average length and average caliper. They are erect and have numerous single and branched scented stipitate glands, with a few prickles. Their color is near Strong Yellow Green, 2.5GY6/8.

Before the calyx breaks, the bud is small in size, of medium length, and ovoid in form, with a conspicuous neck. It has moss in the form of numerous single and branched scented stipitate glands on the surface of the bud, usually with slender foliaceous parts extending beyond the tip of the bud equal to ¼ or more of its length.

As the calyx breaks, the color is creamy white. The inner surface of the sepals carries a fine tomentum; margins are lined with stipitate glands and/or fine hairs.

As the first petal opens, the bud is small to average in size, of medium length, and ovoid to urn-shaped in form. The outer and inner surfaces of the petal are pale yellowish white, with a small area near the base which is near Brilliant Greenish Yellow, 7.5Y9/8.

The bud opens up well, and is not retarded or prevented from opening by cold, hot, wet, or dry weather.

Bloom

When fully open, the bloom is average to large, for miniatures, being from 3 centimeters to 4½ centimeters in diameter. The petalage is double, with usually from 35 to 50 petals, plus 2 to 10 petaloids arranged regularly. The bloom is flat to open at first, becoming flat to open and recurved downward.

At first the petals remain somewhat flat, with tips and/or margins reflexed outward, becoming later at maturity more loose, also flat to open, with tips and/or margins reflexed outward.

Petals

The petals are of medium thickness, with inside slightly velvety and outside slightly shiny to satiny. The outside petals are broadly obovate, while the intermediate petals are obovate and the inside petals narrowly obovate. The colors may be modified by being shaded and/or washed with other colors.

The following describes color values observed in a flower newly opened in the month of August. The plant had been grown outdoors, in Ontario, Calif.

The petals were uniform in coloration, both as respects their inner and outer surfaces and their position as outside petals, intermediate petals, or inner petals. All were off-white, with a small area near the base which was near Brilliant Greenish Yellow, 7.5Y9/8.

The coloration observed in a bloom which had been open for three days, outdoors, in the month of August and having been grown outdoors, in Ontario, Calif., was the same as that of the newly opened flower.

The general color effect of the newly opened flower is creamy white. The bloom after being three days open gives a general color effect of off-white. The petals drop off cleanly, except for petaloids, and are not particularly affected by cold, hot, wet or dry weather.

The flower on the bush in the garden persists for from 3 to 4 days in the month of August, in the locality named.

REPRODUCTIVE ORGANS

The stamens are few to average in number and arranged regularly about the pistils, a few being mixed with petaloids or tucked in the calyx.

The filaments are medium length, their color in the newly opened flowers being near Brilliant Yellow, 5Y9/9, this color fading to pale yellowish white as the flower ages. Most are with anthers.

The anthers are of medium size, all opening approximately at once. The coloration of the anthers along the margins is between Moderate Orange Yellow, 10YR8/10, and Strong Orange Yellow, 7.5YR7/11. Around the point of attachment of the filament the coloration is near Moderate Orange Yellow, 7.5YR8/8.

The pollen is moderate in quantity, and its coloration is between Moderate Orange Yellow, 10YR8/10, and Strong Orange Yellow, 7.5YR7/11.

The pistils are few to average in number, for miniatures, there being approximately 30.

The styles are uneven, of average length, thin caliper, and loosely bunched. They are between off-white and Brilliant Greenish Yellow, 7.5Y9/8, in color.

The stigma is near Brilliant Greenish Yellow, 7.5Y9/8, in color.

The ovaries are usually all enclosed in the calyx.

Hips are of average length, variable in form from ovoid to oblong to globular to pear-shaped. They are near Strong Orange Yellow, 7.5YR7/11, in color, when about half mature. They are prickly, with moderately thick, fleshy walls.

The sepals fall soon. On the plant here described they had all fallen by the time the hips were only half mature.

The seeds are few to average in number, compared to miniatures, generally, and of medium size to large. There are from 2 to 8 seeds.

PLANT

Foliage

The compound leaves usually comprise three to seven leaflets. They are abundant, medium size for miniatures, and from moderately heavy to somewhat leathery and semi-glossy. The leaflets are ovate in shape, with apex acute, base obtuse, and margin irregularly serrate.

The mature foliage, on its upper surface, is generally between Moderate Yellow Green, 7.5GY5/7, and Moderate Olive Green, 7.5GY4/4, in color. The under surface is near Moderate Yellow Green, 5GY5/6, overlaid with heavy gray bloom.

The young foliage, on both its upper and lower surfaces, is a ground color near Strong Yellow Green, 7.5GY6/8, lightly overlaid (but darker near margins) with near Dark Red, 5R3/7.

The rachis is of average size, its upper side grooved, with some stipitate glands on the edges. The under side is sparsely prickly and with stipitate glands.

The stipules are of medium length and medium width, with medium-length points turning out at an angle of usually less than 45°, recurved toward the stem.

The plant displays a better than average resistance to mildew, when compared with other varieties grown under comparable conditions in Ontario, Calif.

Growth

The plant is dwarf, bushy, upright-spreading in habit, much branched, attaining average height for miniatures, but remaining very bushy and compact. It displays a very vigorous growth. The canes are light to medium in caliper.

The main stems are between Moderate Brown, 5YR3/3, and Grayish Brown, 7.5YR3/2, in color. They bear very few large prickles, which are thin, short to medium-length, and almost straight to hooked slightly downward, with short, moderately broad base. There are very few small prickles, and their color as well as the color of the large prickles is from gray to very light brown. There are no hairs or stipitate glands.

The branches are a color between Moderate Yellow Green, 7.5GY5/7, and Moderate Olive Green, 7.5GY4/4, sometimes with corky, brown longitudinal fissures. There are from few to several large prickles which are thin, medium-length to long, almost straight to hooked slightly downward, and with a short moderately broad base. There are from few to several small prickles, and the color of both the large and small prickles is between Strong Yellowish Brown, 10YR5/6, and gray. There are no hairs, but from few to several stipitate glands.

New shoots have a color between Strong Yellow Green, 5GY7/10, and Strong Yellow Green, 5GY6/8. There are several large prickles which are thin, medium-length to long, almost straight to hooked slightly downward, and with moderately short, moderately broad base. There are several small prickles, and both the large and small prickles have a ground color between that of the new shoots and Moderate Yellowish Pink, 7.5R8/6. There are no hairs, but several stipitate glands.

I claim:

1. The hybrid miniature moss rose plant substantially as herein shown and described and having a growth habit appropriate to miniature roses, there being on its peduncles, buds, sepals and hips many single and branched moss-scented stipitate glands, the buds being ovoid to urn-shaped and the flowers, which are double, comprising 35 to 50 petals plus 2 to 10 petaloids, being off-white in color, the plant being characterized further in that it blooms nearly continuously during the growing season, has viable pollen and sets hips.

* * * * *

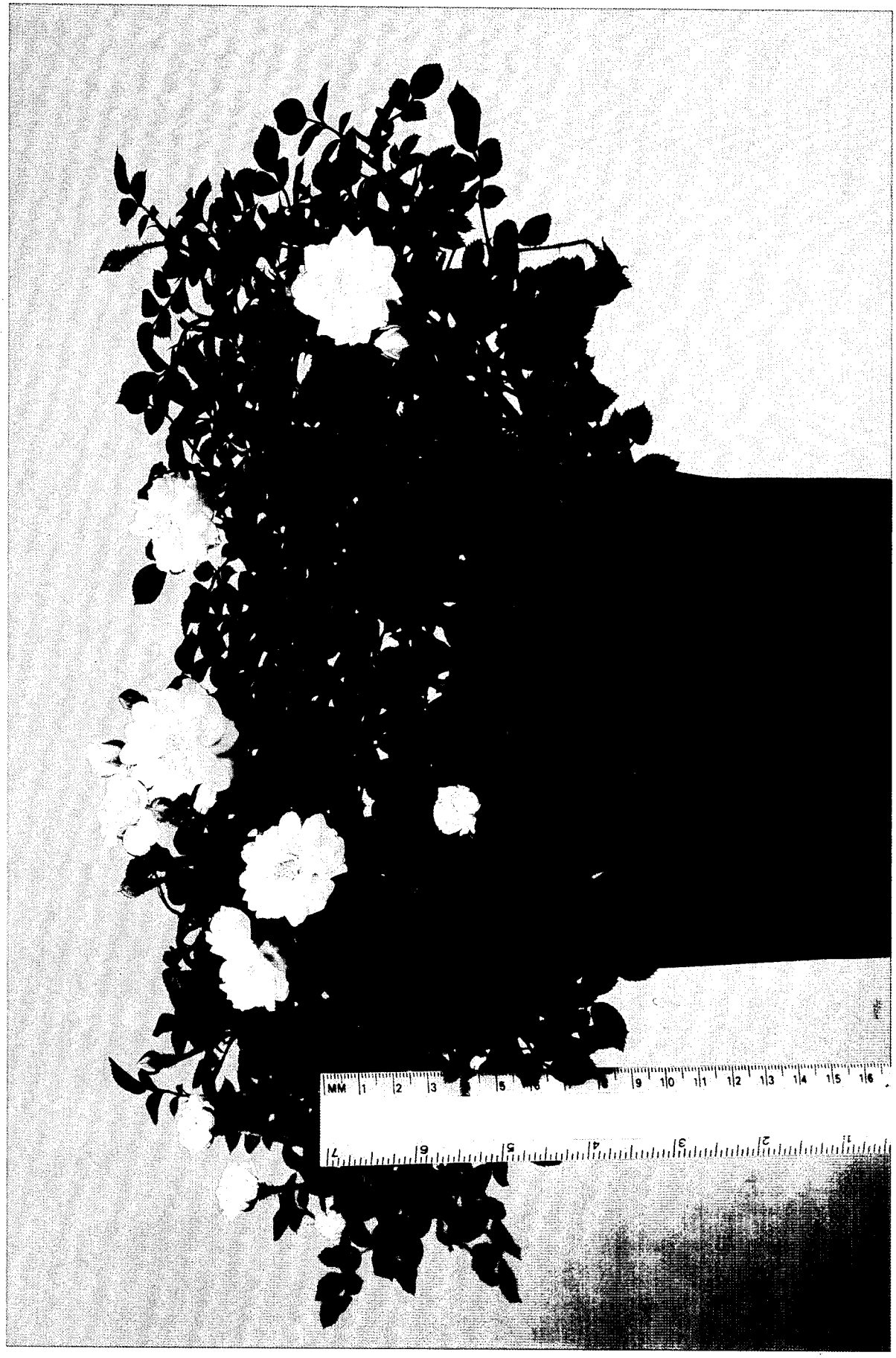
MM